United States Patent [19]

Nelson

[11] 4,118,577
[45] Oct. 3, 1978

[54] 4,5,6-TRINOR-3,7-INTER-M-PHENYLENE PROSTAGLANDIN $A_1$ ANALOGS

[75] Inventor: Norman A. Nelson, Galesburg, Mich.

[73] Assignee: The Upjohn Company, Kalamazoo, Mich.

[21] Appl. No.: 764,359

[22] Filed: Jan. 31, 1977

Related U.S. Application Data

[60] Continuation-in-part of Ser. No. 677,874, Apr. 19, 1976, abandoned, which is a division of Ser. No. 604,158, Aug. 13, 1975, abandoned.

[51] Int. Cl.$^2$ ............................................. C07C 177/00
[52] U.S. Cl. ........................................ 560/53; 562/463
[58] Field of Search ........................... 560/53; 260/520

[56] References Cited

U.S. PATENT DOCUMENTS

| | | | |
|---|---|---|---|
| 3,933,898 | 1/1976 | Nelson | 560/53 |
| 3,933,899 | 1/1976 | Nelson | 560/53 |
| 3,944,595 | 3/1976 | Nelson | 560/53 |

*Primary Examiner*—Paul J. Killos
*Attorney, Agent, or Firm*—Morris L. Nielsen

[57] ABSTRACT

This invention is a group of 4,5,6-trinor-3,7-inter-m-phenylene prostaglandin-type compounds and processes for making them. These compounds are useful for a variety of pharmacological purposes, including hypotensive control and inhibition of platelet aggregation.

A typical formula for a $PGA_1$ type analog is:

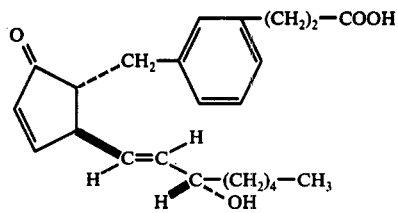

26 Claims, No Drawings

4,5,6-TRINOR-3,7-INTER-M-PHENYLENE PROSTAGLANDIN A₁ ANALOGS

CROSS REFERENCE TO RELATED APPLICATIONS

This application is a continuation-in-part of copending application Ser. No. 677,874 filed Apr. 19, 1976 now abandoned which was a divisional of then co-pending application Serial No. 604,158 filed Aug. 13, 1975 and since abandoned.

BACKGROUND OF THE INVENTION

This invention relates to compositions of matter, and to methods and intermediates for producing them. In particular, the several aspects of this invention relate to novel phenylene analogs of some of the known prostaglandins, i.e. prostaglandin $E_1$ ($PGE_1$), prostaglandin $F_{1\alpha}$ ($PGF_{1\alpha}$), and prostaglandin $A_1$ ($PGA_1$).

The essential material for this application, including the background of the invention, the disclosure of the invention, and the description of the peferred embodiments, including Preparations and Examples, is incorporated by reference from U.S. Pat. No. 4,084,058, issued Apr. 11, 1978, columns 1-65, inclusive, under the provisions of M.P.E.P. 608.01(p).

Previously, certain phenylene-containing prostaglandin analogs were disclosed. See U.S. Pat. Nos. 3,933,897, 3,933,898, and 3,944,595, for a group of phenyleneoxa compounds having a divalent phenylene moiety

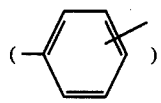

and an oxa oxygen (—O—) in the carboxyl-terminated side chain. See Belgian Pat. No. 820,003, Derwent Farmdoc 22475W for related compounds which are distinguishable from prostaglandins in that they are 11-deoxy compounds.

SUMMARY OF THE INVENTION

It is a purpose of this invention to provide novel phenylene prostaglandin analogs and intermediates and processes for making them.

The novel prostaglandin analogs of this invention each have a meta-substituted divalent phenylene moiety

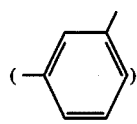

in the carboxyl-terminated side chain of the prostanoic acid structure (I). This phenylene group is in place of three of the six methylene portions of said chain.

Included among the novel inter-m-phenylene compounds of this invention are compounds represented by the formulas:

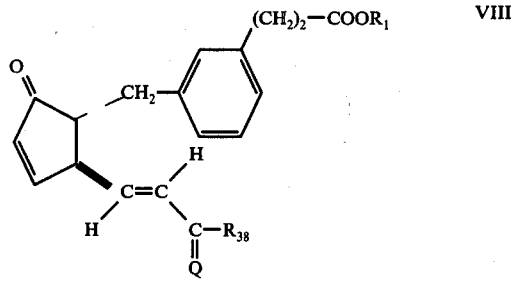

and the mixtures of those compounds and their respective enantiomers represented by the mirror images of the above formulas.

In formula VIII, Q is

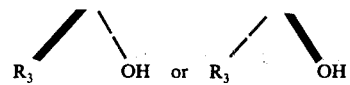

wherein $R_3$ is hydrogen or alkyl or one to 4 carbon atoms, inclusive; $R_1$ is hydrogen, alkyl of one to 12 carbon atoms, inclusive, cycloalkyl of 3 to 10 carbon atoms, inclusive aralkyl of 7 to 12 carbon atoms, inclusive, phenyl, or phenyl substituted with one, 2, or 3 chloro or alkyl of one to 4 carbon atoms, inclusive; and $R_{38}$ is

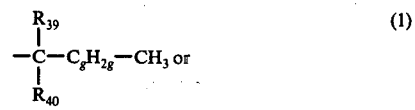

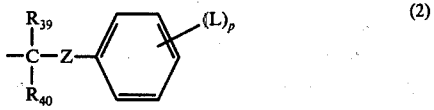

wherein $C_gH_{2g}$ is alkylene of one to 9 carbon atoms, inclusive, with one to 5 carbon atoms, inclusive, in the chain between —$CR_{39}R_{40}$— and terminal methyl, wherein $R_{39}$ and $R_{40}$ are hydrogen, alkyl of one to 4 carbon atoms, inclusive, or fluoro, being the same or different, with the proviso that one of $R_{39}$ and $R_{40}$ is fluoro only when the other is hydrogen or fluoro and the further proviso that neither $R_{39}$ nor $R_{40}$ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between $CR_{39}R_{40}$— and the phenyl ring; and wherein L is alkyl of one to 4 carbon atoms, inclusive, fluoro, chloro, trifluoromethyl, or —$OR_{41}$— wherein $R_{41}$ is alkyl of one to 4 carbon atoms, inclusive, and p is zero, one, 2 or 3, with the proviso that not more than two L's are other than alkyl and when p is 2 or 3 the L's are either the same or different.

There are also included the pharmacologically acceptable salts when $R_1$ is hydrogen.

I claim:

1. An optically active compound of the formula

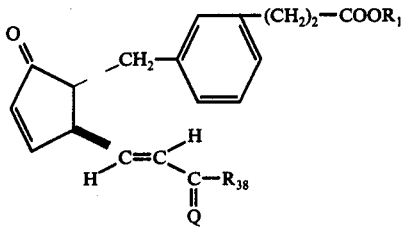

or a mixture comprising that compound and the enantiomer thereof, wherein Q is

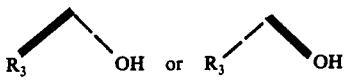

wherein R$_3$ is hydrogen or alkyl of one to 4 carbon atoms, inclusive;
wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; including the pharmacologically acceptable salts thereof when R$_1$ is hydrogen; wherein R$_{38}$ is

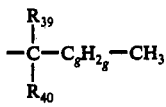

wherein C$_g$H$_{2g}$ is alkylene of one to 9 carbon atoms, inclusive, with one to 5 carbon atoms, inclusive, in the chain between —CR$_{39}$R$_{40}$— and terminal methyl, wherein R$_{39}$ and R$_{40}$ are hydrogen, alkyl of one to 4 carbon atoms, inclusive, or fluoro, being the same or different, with the proviso that one of R$_{39}$ and R$_{40}$ is fluoro only when the other is hydrogen or fluoro.

2. A compound according to claim 1 wherein Q is

3. A compound according to claim 1 wherein Q is

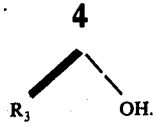

4. A compound according to claim 3 wherein the sum of the number of carbon atoms in R$_3$, R$_{39}$, and R$_{40}$ is less than 7.

5. A compound according to claim 4 wherein C$_g$H$_{2g}$ is alkylene of one to 5 carbon atoms, inclusive.

6. A compound according to claim 5 wherein C$_g$H$_{2g}$ is alkylene of 2, 3, or 4 carbon atoms and R$_{39}$ and R$_{40}$ are hydrogen, methyl, ethyl, or fluoro, being the same or different.

7. A compound according to claim 6 wherein C$_g$H$_{2g}$ is trimethylene.

8. A compound according to claim 7 wherein both R$_{39}$ and R$_{40}$ are hydrogen.

9. A compound according to claim 8 wherein R$_3$ is hydrogen.

10. A compound according to claim 9 wherein R$_1$ is alkyl of one to 12 carbon atoms.

11. 4,5,6-Trinor-3,7-inter-m-phenylene-PGA$_1$, methyl ester, a compound according to claim 10.

12. A compound according to claim 9 wherein R$_1$ is hydrogen or a pharmacologically acceptable cation.

13. 4,5,6-Trinor-3,7-inter-m-phenylene-PGA$_1$, a compound according to claim 12.

14. A compound according to claim 8 wherein R$_3$ is methyl.

15. A compound according to claim 7 wherein one or both of R$_{39}$ and R$_{40}$ are methyl.

16. A compound according to claim 15 wherein R$_3$ is hydrogen.

17. A compound according to claim 16 wherein R$_1$ is alkyl of one to 12 carbon atoms.

18. A compound according to claim 16 wherein R$_1$ is hydrogen or a pharmacologically acceptable cation.

19. 4,5,6-Trinor-3,7-inter-m-phenylene-16-methyl-PGA$_1$, a compound according to claim 18.

20. 4,5,6-Trinor-2,7-inter-m-phenylene-16,16-dimethyl-PGA$_1$, a compound according to claim 18.

21. A compound according to claim 7 wherein one or both of R$_{39}$ and R$_{40}$ are fluoro.

22. A compound according to claim 21 wherein R$_3$ is hydrogen.

23. A compound according to claim 22 wherein R$_1$ is alkyl of one to 12 carbon atoms.

24. A compound according to claim 22 wherein R$_1$ is hydrogen or a pharmacologically acceptable cation.

25. 4,5,6-Trinor-3,7-inter-m-phenylene-16-fluoro-PGA$_1$, a compound according to claim 24.

26. 4,5,6-Trinor-3,7-inter-m-phenylene-16,16-difluoro-PGA$_1$, a compound according to claim 24.

* * * * *